United States Patent [19]

Pratt

[11] 4,180,506

[45] Dec. 25, 1979

[54] 6β-BROMO PENICILLANIC ACID

[76] Inventor: Rex Pratt, 16 Brooks La., Portland, Conn. 06480

[21] Appl. No.: 870,398

[22] Filed: Jan. 18, 1978

[51] Int. Cl.² ........................................ C07D 277/04
[52] U.S. Cl. ................................ 260/245.2; 424/270
[58] Field of Search ............................ 260/306.7 C

[56] References Cited

PUBLICATIONS

Pratt et al., Proc. Natl. Acad. Sci. 75, No. 9, pp. 4145–4149, Sep. (1978).
Loosemore et al., J. Org. Chem. 43, 3611, (1978).
Cephalosporins and Penicillins, pp. 96–105, Academic Press (1972) edited by Flynn.
Clayton, J. Chem. Soc. (C) pp. 2123–2127 (1969).

*Primary Examiner*—Nicholas S. Rizzo
*Attorney, Agent, or Firm*—Hesna J. Pfeiffer; Julian S. Levitt

[57] ABSTRACT

6β-Bromo penicillanic acid is a novel compound which is an antibacterial agent as well as a potent β-lactamase inhibitor.

1 Claim, No Drawings

6β-BROMO PENICILLANIC ACID

RELATIONSHIP TO THE PRIOR ART

Brominated penicillanic acids are described in the literature, see J. P. Clayton, J. Chem. Soc. C, 2123–2127 (1969). The compound prepared in that reference is the 6,6-dibromo penicillanic acid, which did not show any significant antibacterial activity.

DESCRIPTION OF THE INVENTION

It has now been found that the compound 6β-bromo penicillanic acid, prepared via the 6,6-dibromopenicillanic acid of the prior art possesses both antibacterial and β-lactamase inhibitory activities. The compound is therefore valuable as an antibiotic agent in humans or animals against various gram positive and gram negative bacteria. It is also useful in combination with other penicillins and cephalosporins which are susceptible to β-lactamase degradation, such as benzyl penicillin and ampicillin.

SPECIFIC EMBODIMENTS OF THE INVENTION

EXAMPLE 1

Preparation of 6β-Bromo Penicillanic Acid 0.5 G. samples of 6,6-dibromopenicillanic acid [prepared by the method of Clayton, J.C.S. C 2123 (1969)] dissolved in 50 ml. dioxane (freshly distilled from sodium) to which had been added 1.8 g. of $Na_2HPO_4.7H_2O$ and 0.1 g. of 10% Pd/C were hydrogenated at room temperature and room pressure for 2 hours.

The filtered solution was evaporated to dryness under reduced pressure.

The residue was extracted with ether and the ether solution dried over $MgSO_4$ and evaporated under reduced pressure.

This gives a mixture of 6α-bromo penicillanic acid and 6β-bromo penicillanic acid containing 28±5% of the latter (estimated from integration of the NMR spectrum described below) in about 50% total yield.

The free acid mixture, a gum, can be converted into a solid sodium salt mixture by its dissolution in one equivalent of sodium bicarbonate solution followed by freeze drying of the resulting solution.

A solid N,N'-dibenzylethylenediamine (DBED) salt mixture can be obtained by adding one equivalent of the amine to a solution of the acids in ether.

Neither of the above transformations alters the epimeric composition of the mixture.

The epimeric composition is clear from NMR spectra of the above derivatives; for example, that of the sodium salt in $D_2O$ contains the spectrum of 6α-bromopenicillinate (8.52τ(s), 8.42τ(s): C-2 methyl groups; 5.71τ(s): C-3 hydrogen; 4.90τ(d) J=1.5 Hz: C-6 hydrogen; 4.55τ(d) J=1.5 Hz: C-5 hydrogen) as well as the following: 8.50τ(s), 8.37τ(s), 5.76τ(s) and the ab quartet 4.44, 4.39τ(J=3.7 Hz).

The latter spectrum is that of 6β-bromo penicillinate and integration of the spectrum gives the epimer composition quoted above. For chemical analysis the free acid mixture was converted to a p-bromophenacyl ester mixture by the method of Bamberg et al. [Acta Chim. Scand. 21:2210 (1967)] which was purified by elution with chloroform from a silica gel column.

The ester mixture, of unchanged epimeric composition by NMR, analyzed as follows:

Calculated for $C_{16}H_{15}Br_2NO_4S$: C, 40.25; H, 3.27; N, 3.11; Br, 33.60. Found: C, 40.28; H, 3.17; N, 2.94; Br, 33.49.

In comparison the pure 6α-bromo ester obtained by exterification as above of the pure 6α-bromo penicillanic acid prepared by the method of Testa et al. [JOC 27: 2668 (1962)] analyzed as follows:

C, 40.35; H, 3.09; N, 3.28; Br, 33.20.

Hydrogenation of 6,6-dibromo penicillanic acid over 10% Pd/C in aqueous solution in the presence of $Na_2HPO_4$ gives on freeze drying a mixture of the sodium salt of the epimers of 6-bromo penicillanic acid containing about 10% β.

EXAMPLE 2

β-Lactamase Inhibition

The epimer mixture described above either as the free acids or their salts are potent irreversible inhibitors of β-lactamases. This is shown in the table below:

| Enzyme | Residual activity vs. benzyl penicillin after 1 hour as 6β-bromopenicillanic acid to enzyme ratios* | | |
|---|---|---|---|
| | 0.7/1 | 10/1 | 100/1 |
| B. cereus 569/H/9 β-Lactamase I | 36 | 0 | 0 |
| E. coli w 3310 (RTEM) | 100 | 90 | 20 |
| S. aureus (strain unknown) | 100 | 70 | 0 |
| B. licheniformis | 50 | 0 | 0 |

*The enzyme concentrations were 0.2μ molar in all cases.

Comparison of the variation of the inhibitory power of the epimer mixture with content of the β-epimer (Table below) shows clearly that the inhibitor is the 6β-bromopenicillanic acid.

Correlation between β-lactamase inhibition and 6β-bromopenicillanic acid content in bromopenicillanic acid mixtures:

| Sample preparation | % 6β-bromo-penicillanic acid* | % Inhibition of B. cereus β-lactamase I+ |
|---|---|---|
| Diazotization of 6β-aminopenicillanic acid (Method of Testa et al.) | 0 | 0 |
| Hydrogenation of 6,6-Di-bromopenicillanic acid in $H_2O$ | 12 ± 2 | 9 ± 2 |
| Hydrogenation of 6,6-Di-bromopenicillanic acid in dioxane | 28 ± 5 | 27 ± 3 |

*from intergration of NMR spectrum
+Assuming a 1:1 enzyme inhibitor interaction

EXAMPLE 3

Potentiation of Benzyl Penicillin and Ampicillin by the DBED salt of 6-Bromopenicillanic acid Subinhibitory concentrations of the DBED salt of 6-bromo-penicillanic acid (6BPA) markedly potentiated the activity of benzylpenicillin (Pen G) in the presence of $10^4$ units/ml of penicillinase (Difco) in a bilayer agar diffusion test. Using *Vibrio percolans* MB-1272 as the assay organism, the synergistic effect obtained with the 6 BPA salt was approximately 64-fold greater on a weight basis than that observed with a clavulanic acid control.

In a second type of in vitro test, the presence of a subinhibitory concentration of the 6 BPA salt potentiated Pen G and ampicillin 64- and 32-fold respectively, as estimated by regression curves of each antibiotic alone. The results were seen against two penicillinase-producing animal-pathogenic strains of *Staphylococcus aureus* in disc agar diffusion tests.

These two in vitro assays are described below, together with the results in Tables 1 and 2, respectively.

The *Vibrio percolans* test was run by adding Pen G and Penase to separate 10 ml agar layers at 5 µg/ml and $10^4$ units/ml respectively. 6 BPA was applied to the Penase layer in the form of ½" diameter antibiotic discs saturated with serial 2-fold dilutions ranging from 0.25-4.0 ug/ml. This range was chosen to represent ¼-1/64 of the minimum inhibition zone-producing concentrations (MZC) of 6 BPA vs MB-1272 in the absence of Pen G. The 6 BPA-containing discs were permitted to diffuse into the Penase layer for 4 hours at 2°-5° C. after which the discs were removed, the Pen G layer added, and surface inoculated by means of a cotton swab saturated with an overnight culture of MB-1272 diluted to 60% transmission at 660 nm. After overnight incubation at 28° C., plates were examined for synergism of Pen G as signified by the presence of zones of inhibition in the areas in which 6 BPA had diffused.

The *Staphylococcus aureus* assay consisted of a standard disc agar diffusion test in which nutrient agar +0.2% yeast extract (NBY) at 45° was seeded with 3.3% of an overnight culture in NBY of either *S. aureus* MB-3648 or MB-3649, adjusted to 60% transmission at 660 nm. Antibiotic paper discs of ½" diameter were saturated with distilled water solutions of antibiotics. All broths and agar plates were incubated 16–18 hours at 37° C.

TABLE 1

In Vitro Potentiation of Benzylpenicillin (Pen G) in the Presence of Penicillinase by the DBED Salt of 6-Bromo-penicillanic Acid (6 BPA)
Zones of Inhibition, mm vs. V. percolans MB-1272

| Antibiotic, µg/ml | | Antibiotic Alone | Antibiotic + Penase | Antibiotic + Penase + Pen G | Penase + Pen G Alone |
|---|---|---|---|---|---|
| 6 BPA | 31 | 23 | 24 | Not Tested (NT) | 0 |
| 6 BPA | 16 | 12 | 11 | NT | 0 |
| 6 BPA | 8 | 0 | 0 | NT | 0 |
| 6 BPA | 4 | 0 | 0 | 37 | 0 |
| 6 BPA | 2 | 0 | 0 | 31 | 0 |
| 6 BPA | 1 | 0 | 0 | 26 | 0 |
| 6 BPA | 0.5 | 0 | 0 | 23 | 0 |
| 6 BPA | 0.25 | 0 | 0 | 15 | 0 |
| 6 BPA | 0.125 | 0 | 0 | 0 | 0 |
| Clavulanic Acid | 31 | 20 | 21 | 21 | 0 |
| Clavulanic Acid | 16 | 8 | 10 | 10 | 0 |
| Clavulanic Acid | 8 | 0 | 0 | 0 | 0 |
| Clavulanic Acid | 4 | 0 | 0 | 0 | 0 |
| Clavulanic Acid | 2 | 0 | 0 | 0 | 0 |
| Clavulanic Acid | 1 | 0 | 0 | 0 | 0 |

Table 1 shows that it required 64 times as much clavulanic acid (16 µg/ml) to produce a zone of inhibition in the presence of Pen G and Penase than was needed for 6 BPA (0.25 µg/ml).

TABLE 2

In Vitro Potentiation of Benzylpenicillin G (Pen G) and Ampicillin by 6 BPA vs. Two Pen G-Resistant Strains of *Staphylococcus aureus*

| | | Inhibition Zone Diameters, µg/ml vs. *S. aureus* MB-3648 | | |
|---|---|---|---|---|
| Antibiotic, µg/ml | | Alone | Plus 32 µg/ml 6 BPA[a] | Plus 4 µg/ml Clavulanic Ac[a] |
| Pen G | 1250 | 22 | NT | NT |
| | 625 | 19 | NT | NT |
| | 312 | 16 | NT | NT |
| | 156 | 0 | 22 | 23 |
| | 78 | 0 | 22 | 23 |
| | 39 | 0 | 22 | 21 |
| | 19.5 | 0 | 22 | 19 |
| | 9.8 | 0 | 18 | 18 |
| Pen G | 1250 | 19 | NT | NT |
| | 625 | 16 | NT | NT |
| | 312 | 14 | NT | NT |
| | 156 | 0 | 20 | 21 |
| | 78 | 0 | 20 | 20 |
| | 39 | 0 | 19 | 20 |
| | 19.5 | 0 | 18 | 19 |
| | 9.8 | 0 | 15 | 17 |
| Inhibition Zone Diameters, vs. *S. aureus* MB-3648 | | | | |
| Ampicillin | 1000 | 26 | NT | NT |
| | 500 | 23 | NT | NT |
| | 250 | 20 | 26 | 27 |
| | 125 | 18 | 25 | 27 |
| | 62.5 | 0 | 24 | 26 |
| | 31.3 | 0 | 23 | 23 |

TABLE 2-continued

|  |  |  |  |  |
|---|---|---|---|---|
|  | 15.7 | 0 | 23 | 22 |
|  | Inhibition Zone Diameters, vs. *S. aureus* MB-3649 | | | |
| Ampicillin | 1000 | 25 | NT | NT |
|  | 500 | 20 | NT | NT |
|  | 250 | 18 | 29 | 24 |
|  | 125 | 17 | 24 | 25 |
|  | 62.5 | 0 | 23 | 24 |
|  | 31.3 | 0 | 21 | 23 |
|  | 15.7 | 0 | 19 | 20 |

$^a$Concentrations of 32/μg/ml of 6 BPA and 4 μg/ml of clavulanic acid represented ¼MZC of each substance alone vs either MB-3648 or MB-3649.

Table 2 demonstrates that the presence of ¼ of the minimum zone-inducing concentration (MZC) of either 6BPA or clavulanic acid potentiates Pen G 64-fold and ampicillin 32-fold, as determined by extrapolation on a standard curve.

Methods of Using the 6-β-Bromo Penicillanic Acid

As indicated in the above data, the 6-β-bromo penicillanic acid of this invention possesses antibacterial activity in addition to β-lactamase inhibitory activity. Moreover, it possesses it at levels similar to that of clavulanic acid. Data obtained from in vivo studies on the latter compound, Brown et al., Chem., Common., 266 (1976), and J. Antibiotics, 29 No. 6, 668 (1976); and Cole et al., German Patent Off. No. 2,517,316, published Oct. 23, 1975 illustrates dose levels of clavulanic acid useful as an antibiotic and as a potentiator of other penicillins and cephalosporins. Those dose levels are useful in illustrating the levels at which 6-β- bromo penicillanic acid can be used.

For instance, the combination of 6-β-bromo penicillanic acid and other β-lactam antibiotics are employed in ratios of from 10:1 to 1:10, and preferably 3:1 to 1:3. Single dosage forms can be prepared having between 50-1500 mg. active ingredients and preferably between 100-1000 mg. active ingredients. These dosage forms can be administered to humans so that between 50-6000 mg. per day are given, preferably between 500-3000 mg. per day. Specific combinations within these ranges can be easily prepared using techniques in the literature, of the 6-bromo penicillanic acid and commercial β-lactam antibiotics such as benzyl penicillin and ampicillin.

Having described this invention, what is claimed is:
1. 6-β-Bromo penicillanic acid.
* * * * *